United States Patent [19]

Burston

[11] Patent Number: 4,744,624
[45] Date of Patent: May 17, 1988

[54] OPTICAL FIBRE ASSEMBLY FOR TRANSMITTING HIGH ENERGY LASER RADIATION

[75] Inventor: Ronald J. Burston, Barassie, Scotland

[73] Assignee: Pilkington, Medical Systems, Ltd., Clydebank, Scotland

[21] Appl. No.: 806,788

[22] Filed: Dec. 9, 1985

[30] Foreign Application Priority Data

Jul. 4, 1985 [GB] United Kingdom ............... 8516999

[51] Int. Cl.⁴ .................................. G02B 6/36
[52] U.S. Cl. ...................... 350/96.20; 350/96.10; 350/96.26
[58] Field of Search ............ 350/96.10, 96.15, 96.18, 350/96.20, 96.24, 96.26, 96.29, 96.30

[56] References Cited

U.S. PATENT DOCUMENTS

| 4,281,891 | 8/1981 | Shinohara et al. | 350/96.18 |
| 4,421,382 | 12/1983 | Doi et al. | 350/96.20 |
| 4,503,853 | 3/1985 | Ota et al. | 350/96.20 X |
| 4,537,193 | 8/1985 | Tanner | 350/96.20 X |
| 4,550,240 | 10/1985 | Toida et al. | 350/96.10 X |
| 4,669,819 | 6/1987 | Hengst et al. | 350/96.20 |

FOREIGN PATENT DOCUMENTS

| 3241718 | 5/1984 | Fed. Rep. of Germany | 350/96.20 |
| 56-107205 | 8/1981 | Japan | 350/96.20 |
| 59-104606 | 6/1984 | Japan | 350/96.20 |

Primary Examiner—John Lee
Attorney, Agent, or Firm—Stephen G. Rudisill

[57] ABSTRACT

An optical fibre assembly (10) for transmitting high energy laser radiation comprises a tubular moulded plastics handle (1) having a tubular metallic termination (2) for engagement with a laser radiation source. The other end of handle (1) is connected by a heat shrunk plastics sleeve (6) to a length of plastics tubing (4) the distal end of which incorporates an end formation (5), and a single plastics coated glass cored optical fibre (3) extends through the interior of termination (2), handle (1), plastics tube (4) and termination (5). The assembly (10) is easy and inexpensive to manufacture because of the simplicity of components and assembly thereof and enables the assembly (10) to be used on a once-and-for-all basis, i.e., assembly (10) is disposable.

6 Claims, 1 Drawing Sheet

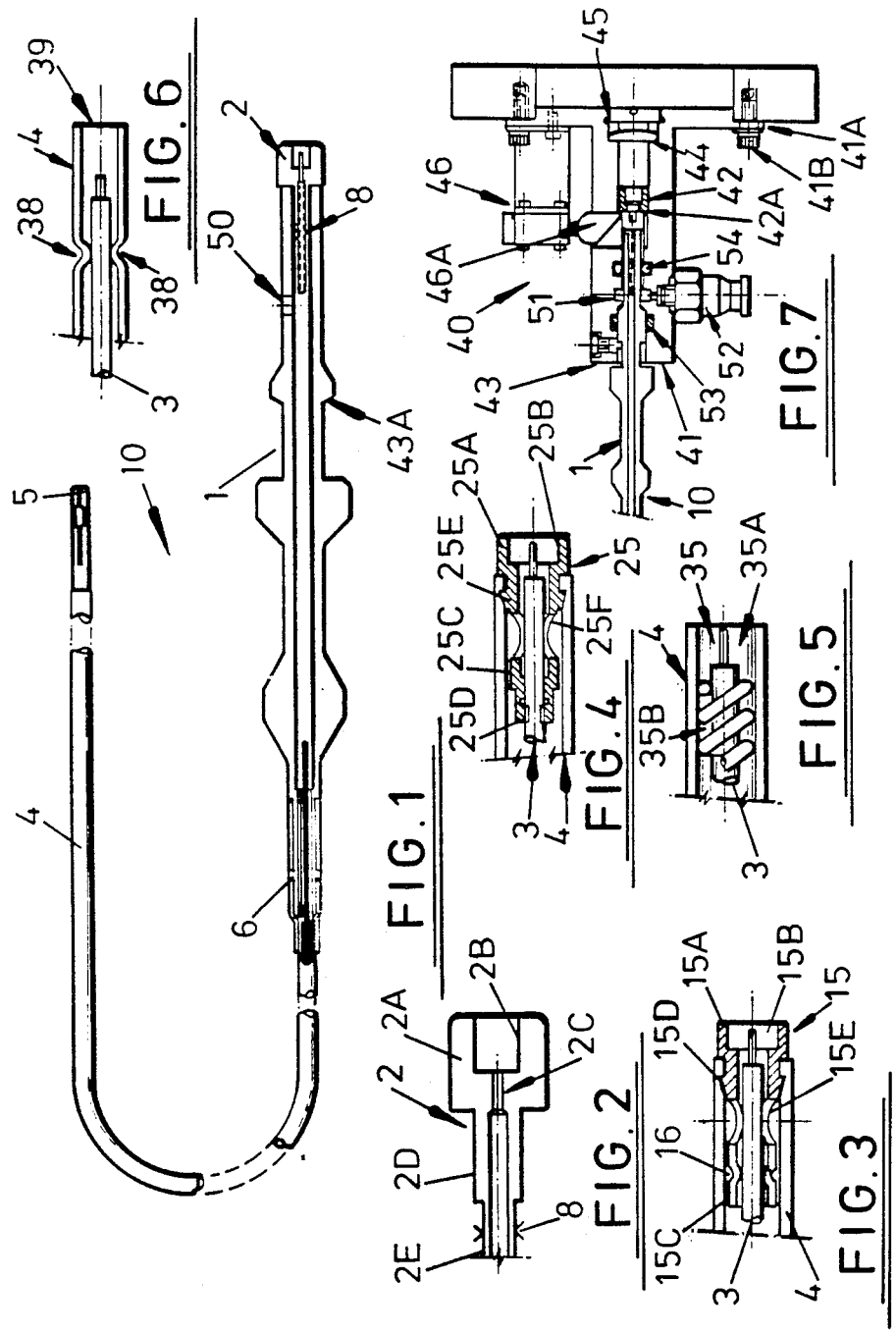

OPTICAL FIBRE ASSEMBLY FOR TRANSMITTING HIGH ENERGY LASER RADIATION

This invention relates to an optical fibre assembly for transmitting high energy laser radiation.

High energy laser radiation is being utilised increasingly in medical work, being delivered to the site to be irradiated by an optical fibre assembly dimensioned externally to fit within an endoscope and being connected to a laser radiation source. Low energy laser radiation is also needed in medical work, primarily for illumination purposes, but whereas low energy radiation may be transmitted by an optical fibre assembly incorporating a fibre bundle, high energy laser radiation is required to be transmitted by a single fibre, and the coupling of that fibre to the laser radiation source is critical if the fibre is to have any usable lifespan. Furthermore, in medical work, sterilization of the optical fibre assembly is critically important if cross contamination of patients is to be avoided.

It is an object of the present invention to provide an optical fibre assembly for transmitting high energy laser radiation, and which is sufficiently easy and inexpensive to manufacture as to permit use on a once-and-for-all basis, whereby such assemblies may be pre-sterilized.

According to a first aspect the present invention provides an optical fibre assembly for transmitting high energy laser radiation, said assembly comprising a tubular moulded plastics handle to which is fitted at one end a tubular metallic termination and at the other end a length of plastics tubing, the distal end of the tubing incorporating an end formation, a single plastics-coated glass-cored optical fibre extending through the interior of the termination, the handle, the tubing and the end formation and being secured to the termination, the plastics tubing being a sliding fit within the bore of the handle and being secured to the handle by a heat shrunk plastics sleeve, the fibre being cleaved at each end and accurately located with respect to the termination by a crimp secural of the termination to the plastics coating of the fibre.

The end formation may be created by pre-crimping the plastics tubing or it may be a separate member capable of centralizing the single fibre in the plastics tubing.

The fibre assembly of the present invention is easy and inexpensive to manufacture in that only one component is required to be made of metal (e.g. a brass termination), the others being made of plastics such as PTFE or polysulphane, and assembly of the components is relatively simple because the plastics tubing is a sliding fit within the bore of the handle. Thus, during assembly, one end of the fibre is crimp connected to the termination whereafter the handle is fed over the length of the fibre into engagement with the termination. The length of tubing is then fed over the fibre and slid into the bore of the handle. When the end formation is a separate member this sliding movement is sufficient to expose the distal end of the fibre which is fitted to the end member and thereafter the tubing is slid in the reverse direction into engagement with the end member. The heat shrinkable plastics sleeve is fitted and heat shrunk thereafter to the handle in order to secure the tubing in its final position.

The optical fibre conveniently has a hard silica core and may have a plastics cladding over which is a relatively thick plastics coating which provides the basis for the crimp secural. One suitable form of fibre is manufactured by Ensign Bickford Inc. of 660 Hopmeadow Street, Simsbury, Conn., U.S.A. under product reference number HC - 412T.

Preferably the handle is provided on its outer surface with a flange disposed at a predetermined distance from said termination whereby the handle is capable of being resiliently urged to seat the termination against a mechanical stop associated with a laser radiation source in order precisely to locate the cleaved fibre end at the focal point of the incoming laser radiation. In this connection it will be understood that in order to couple high energy laser radiation from a source into an optical fibre assembly it is necessary to pass the collimated laser beam through a focussing lens and to locate the fibre end at the focal point such that laser radiation is incident only on the core portion of the single fibre.

In accordance with a second aspect of the invention there is provided apparatus for coupling an optical fibre assembly in accordance with the first aspect of the present invention to a laser radiation source, said apparatus comprising a member defining a socket for receiving the handle and termination of said assembly, an abutment collar being fixedly mounted in said socket and having an abutment surface located at a predetermined distance from a focussing lens mounted on said member, the optical axis of said lens being aligned with the longitudinal axis of said socket, said member being provided with means for securing the member to the housing of a laser radiation source.

Conveniently an electrical interlock device incorporating a microswitch is mounted on said member and is arranged for connection to enable and/or disable a said laser radiation source according to the presence or absence of a said fibre assembly fitted to said socket with said termination in abutment with said abutment surface.

An embodiment of the present invention will now be described by way of example with reference to the accompanying drawings, in which:

FIG. 1 illustrates an optical fibre assembly according to the present invention;

FIG. 2 illustrates a detail of the FIG. 1 assembly to a greater scale;

FIGS. 3, 4 and 5 illustrate alternative forms of another detail of the FIG. 1 assembly;

FIG. 6 illustrates a modified form of a detail of the FIG. 1 assembly; and

FIG. 7 illustrates the assembly of FIG. 1 fitted to apparatus according to the second aspect of the invention.

As is shown in FIG. 1 an optical fibre assembly 10 comprises a tubular moulded plastics handle 1 to which there is fitted at one end a tubular metallic termination 2, this termination 2 being illustrated in greater detail in FIG. 2. A length of plastics tubing 4 is fitted to the other end of the handle 1, tubing 4 being a sliding fit within the bore 7 of handle 1, the final location of tubing 4 with respect to handle 1 being preserved by a heat shrunk plastics sleeve 6 overlapping part of handle 1 and part of tubing 4. At the distal end of tubing 4 there is provided an end member 5, alternative forms of which are illustrated more clearly in FIGS. 3, 4 and 5 respectively, and secured to termination 2 and to member 5 and extending within tubing 4, handle 1, and member 2 there is a plastics coated glass cored optical fibre 3. The fibre 3 is secured to termination 2 by crimping at location 8, this crimping being such that the thin walled portion of termination 2 is deformed into mechanical engagement with the plastics coating of fibre 3 but with insufficient deformation to affect the optical properties of the fibre. At its other end optical fibre 3 is secured to end member 5 in any one of the configurations to be explained with reference to FIGS. 3, 4 and 5. Each end of the fibre 3 is free of plastics coating for a very short distance and the fibre end faces are each cleaved.

Termination 2 is shown in greater detail in FIG. 2 from which it will be seen that the termination is of tubular structure comprising a head portion 2A with a principal recess 2B into which the cleaved end of fibre 3 protrudes, the head portion incorporating a bore 2C for locating the fibre 3 concentrically and integral with head portion 2A is a tubular shank 2D dimensioned to be an interference fit with the bore 7 of handle 1, a thin walled shank portion 2E being integral with shank 2D and incorporating crimp location 8.

In order to assemble fibre 3 to termination 2 the plastics coating is initially stripped back from the end of the fibre which is thereafter fitted into termination 2 until the cleaved end face of the fibre is precisely located axially within recess 2B and thereafter a crimp tool (not shown) is applied to thin walled portion 2E to crimp termination 2 onto the plastics coating of fibre 3. Handle 1 is thereafter slid along the length of the fibre 3 and forced into engagement with shank 2D which conveniently may be provided with tooth-like protrusions to prevent disengagement. The required length of tubing 4 is thereafter slid over the free end of fibre 3 and caused to slide along bore 7 of handle 1 until such time as the free end of fibre 3 protrudes from tubing 4. Thereafter end member 5 is secured to the fibre 3 and tubing 4 is slid in the reverse direction with respect to handle 1 into engagement with end member 5. Finally, a length of heat shrinkable plastic sleeving is slid along the exterior of tubing 4 to overlap with part of handle 1 and part of plastics tubing 4, heat thereafter being applied in order to shrink sleeve 6 into place.

As is shown in FIG. 3 one form of end member 15 comprises a head portion 15A with a recess 15B into which the cleaved end of fibre 3 is located, head portion 15A being integral with a relatively thin walled shank portion 15C which at location 16 is deformed by crimping so as to engage with the plastics coating of fibre 3, the outer surface of head portion 15A being provided with teeth 15D which engage with the plastics tubing 4 in order to secure tubing 4 in position.

As is shown in FIG. 4 another form of end member 25 comprises a head portion 25A having a recess 25B for receiving the cleaved end of the fibre 3 and a shank portion 25C terminating in inwardly extending teeth 25D which are arranged to grip the plastics coating of fibre 3 in screw-thread-like manner. The outer surface of head portion 25A is provided with teeth 25E for engagement with plastics tubing 4.

As shown in FIG. 5 a still further form of end member 35 is in the form of a helical spring externally dimensioned to fit within and grip plastics tubing 4 and internally dimensioned to receive and grip the plastics coating of fibre 3. In this case tubing 4 is axially extended beyond end member 35 in order to provide a recess 35A for the cleaved end of fibre 3.

FIG. 6 illustrates a modified form of the distal end retention arrangement for the fibre 3 in which the plastics tubing 4 is pre-crimped radially with four indentations 38 leaving an axially disposed gap sufficient to centrally locate the end of fibre 3 without gripping the fibre. With this arrangement retention of the tubing 4 is effected solely at the handle 1 by means of the heat shrink sleeve 6 and tubing 4 is axially extended beyond end formation 38 to provide a recess 39 for the cleaved end of fibre 3. The exact axial length of recess 39 is relatively unimportant and may be sufficiently oversize to provide protection against damage during transit of the assembly 10 in which case it is preferred that the user cut off the unwanted length of tubing 4 prior to use of the assembly 10, this being easy to effect because tubing 4 is made of plastics. Furthermore, with the FIG. 6 arrangement during assembly of the components it will be appreciated that there is no requirement to reverse slide the tubing 4 since there is no separate end member per se and, of course, there is no danger of the end member becoming disengaged and lost during use of the assembly 10 if the end member is absent.

As is shown in FIG. 7 assembly 10 is arranged to be fitted to a laser source (not shown) by way of an assembly 40 comprising a socket member 41 into which the nose portion of handle 1 is a sliding fit. Within the socket of member 41 there is provided an end stop 42 having an abutment surface 42A against which termination 2 is resiliently urged by means of spring loaded detent 43 mounted in member 41 and engaging a radially extending shoulder 43A on handle 1. The end stop 42 is itself axially apertured and surface 42A is factory set at a critical distance from a focussing lens 44 which is held by mounts 45 such that its optical axis is precisely aligned with the longitudinal axis of the socket formed within member 41.

Member 41 is provided with a termination flange 41A incorporating X,Y, adjustment means 41B whereby the flange is capable of being secured to the housing of a laser radiation source (not shown) so that the optical axis of lens 44 is precisely aligned with the received radiation axis.

An electrical interlock device 46 is fitted to member 41 and incorporates a microswitch 46A which is actuated by the termination 2 and interlock device 46 is arranged, in use, to enable the laser source when assembly 10 is fitted to member 41 and to disable the laser radiation source when assembly 10 is not so fitted.

It will be appreciated that in a medical environment the site to which radiation is to be delivered incorporates a variety of liquids which in relation to the optical fibre 3 are contaminants and in order to keep the cleaved fibre end face free of such contaminants it is desirable to surround the fibre end face with one or more jets of inert gas. To provide such gas jetting, handle 1 is provided with aperture 50 which, when the handle is fitted to member 41, is aligned with an annular channel 51 to which fitting 52 provides gas from a supply (not shown). Axial flow of gas within member 41 is prevented by O-ring seals 53, 54, and gas entering handle 1 flows along the annular channel formed between the fibre 3 and the interior of tubing 4 and emerges from the end of assembly 10 via end member 5. For this purpose the end member 15 (FIG. 3) is provided with a cut-out portion 15E; the end member 25 (FIG. 4) is provided with a cut-out portion 25F; and the end member 35 (FIG. 5) is provided with separated coils so that a helical passageway 35B is provided. In the FIG. 6 case the circumferential regions between the four indentations 38 provide through passageways for gas flow.

The assembly 10 which has been described is sufficiently cheap and easy to manufacture to be used on a once-and-for-all basis and is easily coiled and packaged and sterilized, such as by ethylene oxide sterilization.

What is claimed is:

1. An optical fibre assembly for transmitting high energy laser radiation, said assembly comprising a tubular moulded plastics handle to which is fitted at one end a tubular metallic termination and at the other end a length of plastics tubing adapted to fit within an endoscope, the distal end of the tubing incorporating an end formation within the bore of the tubing, a single plastics-coated glass-cored optical fibre extending through the interior of the termination, the handle, the tubing and the end formation and being secured to the termination, the plastics tubing being a sliding fit within the bore of the handle to enable location of the end formation on the fibre and being secured to the handle by a heat shrunk plastics sleeve, the fibre being cleaved at each end and accurately located with respect to the termination by a crimp secural of the termination to the plastic coating of the fibre, the fibre diameter being smaller than the bore of the tubing to thereby establish a channel between the fibre and the tubing and the end formation being provided with a thru passageway communicating with said channel whereby, in use, gas can be transmitted along said channel and thru said passageway to free the cleaved fibre end face of contaminants.

2. An assembly as claimed in claim 1, wherein the end formation is in the form of a separate member releasably secured to the distal end of the plastics tubing.

3. An assembly as claimed in claim 1, wherein the end formation comprises a pre-crimped portion of the plastics tubing at its distal end.

4. An assembly as claimed in any preceding claim, wherein the only component which is made of metal is the end termination.

5. An assembly as claimed in claim 4, wherein the end termination is made of brass.

6. An assembly as claimed in claim 1, wherein the handle is provided on its outer surface with a flange disposed at a predetermined distance from the end termination whereby the handle is capable of being resiliently urged to seat the termination against a mechanical stop associated with a laser radiation source in order to precisely locate the cleaved fibre end at the focal point of the radiation emitted by the radiation source.

* * * * *